United States Patent [19]

Molteno

[11] Patent Number: 4,750,901
[45] Date of Patent: Jun. 14, 1988

[54] IMPLANT FOR DRAINAGE OF AQUEOUS HUMOUR

[76] Inventor: Anthony C. B. Molteno, 400 Signal Hill Rd., Dunedin, New Zealand

[21] Appl. No.: 22,100
[22] Filed: Mar. 5, 1987
[30] Foreign Application Priority Data
   Mar. 7, 1986 [NZ] New Zealand ............ 215409
[51] Int. Cl.⁴ .................. A61M 5/00; A61M 35/00
[52] U.S. Cl. .................................. 604/8; 604/294
[58] Field of Search ........................... 604/8–10, 604/294; 623/4

[56] References Cited
U.S. PATENT DOCUMENTS 3,159,161 12/1964 Ness ................................. 604/8
4,457,757 7/1984 Molteno ........................... 604/294
4,521,210 6/1985 Wong .............................. 604/8
4,604,087 8/1986 Joseph ............................. 604/9

Primary Examiner—Ronald L. Frinks
Attorney, Agent, or Firm—Ladas & Parry

[57] ABSTRACT

An implant (1a) for drainage of aqueous humour in glaucoma comprising an episcleral plate (2) having an elevated peripheral ridge (3) and a drainage tube (4) for insertion into the anterior chamber of the eye which has an opening (8) to the upper surface of the episcleral plate (2). A secondary elevated ridge (7) divides the ridged area on the upper surface of the plate (2) into two areas with the opening (8) of the drainage tube (4) located within one area. Preferably the area in which the tube opening (8) is located is significantly smaller than the remaining area of the episcleral plate (2).

7 Claims, 1 Drawing Sheet

IMPLANT FOR DRAINAGE OF AQUEOUS HUMOUR

This invention relates to an implant for drainage of aqueous humour in glaucoma.

I have previously developed a device for the drainage of aqueous humor in glaucoma which is described and claimed in my New Zealand Patent Specification No. 192390. When my original device is inserted into an eye with its tube in the anterior chamber, the plate sutured to the eye and covered by a smooth layer of the patient's tissue known as Tenon's capsule, there is a period of a few days during which the aqueous humour from the eye can be absorbed very easily into the Tenon's tissue overlying the plate. This excess absorbtion causes the pressure within the eye to fall to an unacceptably low level which may result in surgical complications which damage sight.

It is an object of the present invention to provide an implant for drainage of aqueous humour in glaucoma which will overcome or at least significantly reduce the above identified problem.

Accordingly the invention consists in an implant for drainage of aqueous humour in glaucoma, the said implant comprising an episcleral plate having an elevated peripheral ridge, a drainage tube having an opening to the upper surface of the episcleral plate inside the elevated ridge, a secondary elevated ridge rising from the upper surface of the episcleral plate to divide the ridged area on the said upper surface of the plate into two areas with the opening of the drainage tube located within one area.

Preferably the area in which the tube is located is significantly smaller than the remaining area of the episcleral plate.

Preferably the drainage tube can enter through the peripheral ridge with the subsidiary ridge dividing off a comparatively small part of the episcleral plate surrounding the opening with the subsidiary ridge being semi-elliptical or semi-circular in shape.

The prefered configuration has been developed inter alia for manufacturing convenience and the advantage of the invention could be achieved with differing arrangements, for example, with a drainage passage incorporated within the episcleral plate and arrange to have connected thereto a tube leading to the anterior chamber and with a ridge located about the entrance of the drainage passage through the episcleral plate.

It may be desirable to have more than one subsidiary ridge so that in use the bleb cavity created by the implant would be progressively enlarged.

This invention may also broadly be said to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

One preferred form of the invention will now be described with reference to the accompanying drawings in which.

Figure 1:
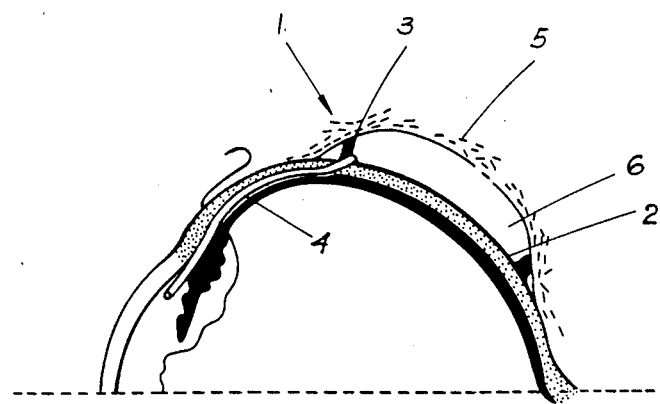
FIG. 1 shows an implant fitted in an eye.

FIG. 1 shows an implant 1 fitted in use. The episcleral plate 2 is appropriately positioned on the globe and secured by suitable sutures passed thorugh anterior suture holes. The episcleral plate 2 has an elevated peripheral ridge 3 and a silicone drainage tube 4 which leads from the upper surface of the episcleral plate 2 to the anterior chamber in the eye. The fibrovascular bleb wall 5 in association with the episcleral plate 2 defines the bleb cavity 6.

Once the implant is inserted there is a period of a few days during which the aqueous humour from the eye is absorbed very easily into the Tenon's tissue overlying the plate 2. It is this excess absorbtion which may result in surgical complications which damage sight.

Figure 2:
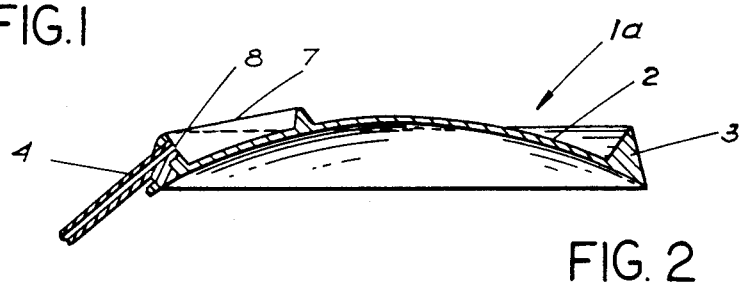
FIG. 2 is a cross section of the modified implant according to the present invention and FIG. 3 is a plan view of FIG. 2.
Figure 3:
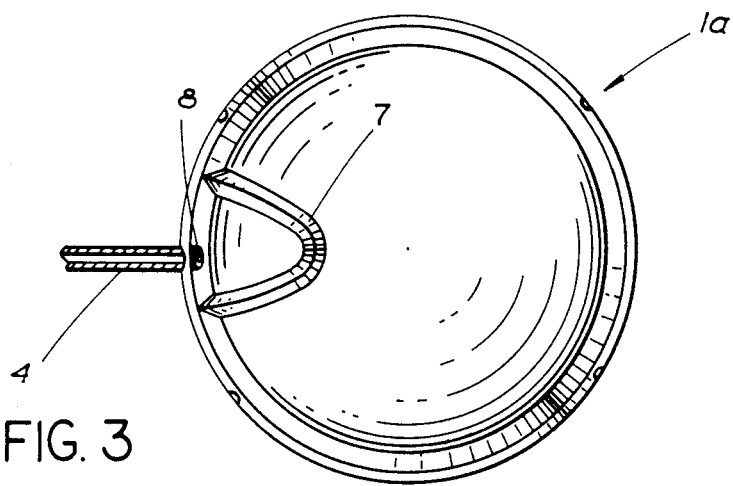

My present modified implant is more particularly illustrated in FIGS. 2 and 3. The implant 1a has the episcleral plate 2 with the peripheral ridge 3 intergrally formed and elevated above the top surface of the episcleral plate. The silicone drainage tube 4 passes through the wall of the ridge 3 and is of a length sufficient to reach the anterior chamber of the eye in a manner illustrated in FIG. 1.

A subsidiary or secondary elevated ridge 7 is located about the entrance 8 of the tube 4 through the ridge 3 to a position above the upper surface of the plate 2 and thus effectively into a first ridged area of the episcleral plate which in use and combination with the Tenon's tissue creates an initial bleb cavity much smaller in area than the total bleb cavity available with the full peripheral ridge of the episcleral plate.

The addition of the subsidiary ridge to the upper surface of the plate 2 around the exit 8 of the tube 4 thus has the effect of providing a pressure sensitive one-way valve effect when the implant according to the present invention is used.

This valve action is brought about by Tenon's tissue covering the episcleral plate 2 and moulding itself into close contact with the circumferential ridge 3 and the subsidiary ridge 7. This ensures that aqueous fluid is drained initially into the smaller cavity defined by a section of the peripheral ridge 3 and the subsidiary ridge 7. Absorbtion of aqueous humour from this is limited by the small area of Tenon's tissue exposed.

Once the eye recovers from the operative interference the increased production of aqueous fluid by the eye raises the pressure within the eye and also within the small bleb cavity causing the overlying Tenon's tissue on a part for all of the subsidiary ridge to be lifted slightly thereby allowing fluid to gain access to the second and large bleb cavity. After a short period of weeks at most, the tissues around the implant form a fibrous capsule which remains permanently distended lifting the Tenon's tissue off the internal ridge and allowing free communication between the interior of the eye and the whole bleb cavity.

The dimensions and height of the subsidiary ridge 7 are important for the following reasons:
1. The force tending to lift the tissue off the subsidiary ridge 7 for any given level of intraocular pressure, depend directly on the area of the cavity enclosed.
2. The height of the subsidiary ridge 7 will likewise have an influence i.e. a higher ridge requiring a somewhat greater elevation of intraocular pressure before acqueous fluid would escape into the main bleb cavity.

The precise behaviour of this device depends critically on the elasticity of Tenon's tissue, how tightly it is stretched over the implant at the end of the operation and the degree of inflammation that develops during the post operative period. These factors vary between differing individuals.

Current clinical experience suggests that the dimensions giving the distance of the outlet from the tube 4 to the furtherest point of the subsidiary ridge 7 to be substantially three millimetres and the height of the subsidiary ridge at its innermost point on the episcleral plate to be approximately 0.75 millimetres would be suitable but the area, height of the ridge, shape of the ridge and contour may well be modified in the light of further clinical experience.

There may be advantages in adding further systems of ridges to further subdivide the plate, that is taking FIG. 3 a third ridge not shown but similar in shape to the ridge 7 could be formed on the outside of ridge 7 so that there would be a second restricted bleb chamber available before the full bleb chamber was exposed. Such an arrangement may have advantages to give a level of operative tolerances which will accommodate behaviour in a range of conditions explained above.

The present disclosure has been confined to a single plate implant although the technique may be applied where there are two episcleral plates connected by a suitable connecting conduit. The present invention would of course generally apply to the first plate, that is the one connected to the eye. It would be feasible to omit the second plate using the present invention, also it would be possible to have ridges on all plates employed in the system.

What I claim is:

1. An implant for drainage of aqueous humour in glaucoma, the said implant comprising an episcleral plate having an elevated peripheral ridge, a drainage tube having an opening to the upper surface of the episcleral plate inside the elevated ridge, a secondary elevated ridge rising from the upper surface of the episcleral plate to divide the ridged area on the said upper surface of the plate into two areas with the opening of the drainage tube located within one area.

2. An implant as claimed in claim 1 wherein the area of the episcleral plate in which the opening to the tube is located is significantly smaller than the remaining ridged area of the episcleral plate.

3. An implant as claimed in claim 1 wherein the secondary elevated ridge extends at either end from the peripheral ridge and describes a path towards the center of the plate to divide off a sector of the episcleral plate spanning substantially forty five degrees.

4. An implant as claimed in claim 3 wherein the secondary ridge describes a substantially semi-elliptic shape.

5. An implant as claimed in claim 3 wherein the distance from the opening to the drainage tube and the point of the subsidiary ridge furtherest removed from the opening to the center of the episcleral plate is approximately substantially 3 millimetres.

6. An implant as claimed in claim 1 wherein the height of the subsidiary ridge at the position closest to the center of the episcleral plate is substantially 0.75 of a millimetre.

7. An implant as claimed in claim 1 wherein the opening to the drainage tube passes through the peripheral ridge on the episcleral plate.

* * * * *